US 7,465,948 B2

(12) United States Patent
Reich et al.

(10) Patent No.: US 7,465,948 B2
(45) Date of Patent: Dec. 16, 2008

(54) SHEET-SURFACE ANALYSER AND METHOD OF ANALYSING A SHEET-SURFACE

(75) Inventors: Michael Reich, Mt. Waverley (AU); Rafik Faltas, Mt. Waverley (AU)

(73) Assignee: Paper Australia Pty Ltd., Mount Waverley, Victoria (AU)

( * ) Notice: Subject to any disclaimer, the term of this patent is extended or adjusted under 35 U.S.C. 154(b) by 97 days.

(21) Appl. No.: 10/572,269

(22) PCT Filed: Sep. 16, 2004

(86) PCT No.: PCT/AU2004/001258

§ 371 (c)(1),
(2), (4) Date: May 22, 2006

(87) PCT Pub. No.: WO2005/026660

PCT Pub. Date: Mar. 24, 2005

(65) Prior Publication Data

US 2007/0035733 A1   Feb. 15, 2007

(30) Foreign Application Priority Data

Sep. 16, 2003   (AU) .............................. 2003905041

(51) Int. Cl.
*G01B 11/30* (2006.01)
(52) U.S. Cl. ............................. 250/559.04; 250/559.41; 250/559.45; 356/239.8; 356/429
(58) Field of Classification Search ............ 250/559.04, 250/559.05, 559.12–559.15, 559.4; 356/600, 356/239.7, 239.8, 429–431
See application file for complete search history.

(56) References Cited

U.S. PATENT DOCUMENTS

| 3,922,093 | A | 11/1975 | Dandliker et al. |
| 4,019,066 | A | 4/1977 | Lucas et al. |
| 4,760,271 | A | 7/1988 | Brenholdt |
| 5,684,707 | A | 11/1997 | Rogowski |
| 5,899,959 | A | 5/1999 | Shields et al. |
| 6,046,828 | A * | 4/2000 | Feng et al. ................... 358/488 |
| 6,411,860 | B1 | 6/2002 | Chen |
| 6,477,892 | B1 | 11/2002 | Lindig |
| 6,529,269 | B1 * | 3/2003 | Sugata ........................ 356/71 |
| 6,629,452 | B2 | 10/2003 | Lindig |
| 7,079,702 | B2 * | 7/2006 | Watanabe et al. ........... 382/274 |
| 2003/0015025 | A1 | 1/2003 | Lindig |
| 2003/0112439 | A1 * | 6/2003 | Nettekoven et al. ......... 356/430 |

FOREIGN PATENT DOCUMENTS

CA   1014638   7/1977

(Continued)

*Primary Examiner*—Georgia Y Epps
*Assistant Examiner*—Tony Ko
(74) *Attorney, Agent, or Firm*—Knoble, Yoshida & Dunleavy

(57) ABSTRACT

The present invention relates to a sheet-surface analyser (10) including illuminating means (32) for casting shadows on the sheet-surface; capturing means (36) for capturing an image of the shadows; analysing means (40) for analysing the captured image to thereby analyse the sheet surface; and curving means (22) for curving the sheet, wherein the illuminating means and the curving means are configured to enable the illuminating means to cast shadows on a curved part of said sheet-surface, and the capturing means is configured to capture said shadow-image.

19 Claims, 15 Drawing Sheets

FOREIGN PATENT DOCUMENTS

| | | |
|---|---|---|
| CA | 1230499 | 12/1987 |
| DE | 19733775 A1 | 2/1999 |
| DE | 19934934 C1 | 6/2001 |
| JP | 9257443 | 10/1997 |
| JP | 2001099629 | 4/2001 |
| WO | 9300566 A1 | 1/1993 |
| WO | WO 93/00566 | 1/1993 |
| WO | 0068638 A1 | 11/2000 |
| WO | 0068666 A1 | 11/2000 |
| WO | 03020445 A1 | 3/2003 |

* cited by examiner

| File Name | Date/Time | M.D. Roughness | C.D. Roughness | Average R |
|---|---|---|---|---|
| Test | 7/16/2003 10:15:04 AM | 94.92 | 98.28 | 96.6 |
| Test | 7/16/2003 10:15:09 AM | 92.96 | 95.86 | 94.41 |
| Test | 7/16/2003 10:15:13 AM | 89.99 | 92.34 | 91.17 |
| Test | 7/16/2003 10:15:18 AM | 90.52 | 90.71 | 90.61 |
| Test | 7/16/2003 10:15:23 AM | 90.14 | 91.64 | 90.89 |
| Ave. Roughness | 91.77 | Rejected value: 96.60 | | |

Fig. 16

| | A | B | C | D | E |
|---|---|---|---|---|---|
| 1 | File Name | Date/Time | M.D. Roughness | C.D. Roughness | Average Roughness |
| 2 | Test | 7/16/2003 10:18 | 89.28 | 94.85 | 92.07 |
| 3 | Test | 7/16/2003 10:18 | 86.76 | 87.95 | 87.35 |
| 4 | Test | 7/16/2003 10:18 | 84.3 | 85.98 | 85.14 |
| 5 | Test | 7/16/2003 10:18 | 84.84 | 87.62 | 86.23 |
| 6 | Test | 7/16/2003 10:18 | 86.33 | 87.04 | 86.68 |
| 7 | Ave. Roughness | 86.35 | Rejected value 92.07 | | |

Fig. 17

SHEET-SURFACE ANALYSER AND METHOD OF ANALYSING A SHEET-SURFACE

FIELD OF THE INVENTION

The present invention relates to a sheet-surface analyser and to a method of analysing a sheet-surface, such as the surface of a paper sheet.

BACKGROUND OF THE INVENTION

The quality of the surface of various types of sheet material is often a very important parameter during production and subsequent processes which add value to the sheet material. As an example, paper products have certain characteristics, such as roughness, pore structure and linting which can significantly impact on production quality and down-stream processing (such as printing). By way of example, the background to this invention is further illustrated below by reference to the importance of roughness in paper products. However, this should not be construed so as to limit the scope of the present invention.

The 'roughness' (or conversely the 'smoothness') of paper is an important property that affects the papers's printability, appearance and texture. Roughness can manifest itself in various ways, such as in the surface profile, texture, pore structure or linting properties of the paper.

Roughness is affected by factors such as the furnish used to make the paper, surfaces with which the paper is contact in during manufacture, applied coating and the calendering process. 'Calendering' is a process used in papermaking to smooth the paper by passing it through one or more nips between two steel rolls, or through one or more nips between one steel and one polymeric or cotton covered roll.

Roughness is commonly measured using laboratory instruments based on the air-leak principle. Air-leak instruments measure roughness by placing a ring on top of the paper surface using a pre-selected force. Pressurised air escapes from the inside of the ring to the atmosphere through the gaps between the paper's surface and the ring. A rougher sheet has more or larger air gaps, and so the flow rate of air lost in this way is increased. The flow rate is measured and used as a basis for determining a roughness value. Three commonly used air-leak instruments include the Bendtsen, Sheffield and Parker Print Surf testers. Such air-leak instruments are commonly employed and relatively quick to use. However, they only provide limited roughness information, and the results are thought to be affected by air escaping through the pores in the sheet as well as through the sheet's surface roughness. The ring can also deform the surface of the paper as the measurement involves contact between the ring and the paper. In addition, air-leak devices do not describe the scale of the roughness, i.e. how the roughness of the sheet varies over the plane of the sheet, and whether this variability is periodic.

Paper roughness is less commonly measured using stylus-based instruments. A stylus is passed over the paper surface and its deviation is measured. Although this technique is capable of providing a three-dimensional description of the paper's roughness, it is rarely used due to it being relatively slow and not sufficiently robust for a paper mill's test room. There is also a possibility that pressure on the stylus will distort the roughness information due to the surface of the sheet being compressed against the stylus surface during measurement.

An alternative to the stylus instrument is to pass a triangulating laser over the paper's surface to determine the deviation of the surface. While the laser does not distort the surface, there is a question over whether the laser detects the paper's surface or a point beneath the paper's surface as light does not perfectly reflect from paper. As with stylus based-instruments, laser-based roughness measurement is slow and not routinely used for quality control purposes.

Paper roughness can also be measured by image analysis of cross-sectional images of paper sheets. This method is accurate, however only a very small area of the surface of the paper can be practically measured in this way. Moreover, specialist equipment and skills are required to perform the analysis.

An alternative approach for measuring paper roughness is described in U.S. Pat. No. 4,019,066. A beam of light is projected onto a moving paper web at a relatively low angle to obliquely illuminate the surface of the paper. Light reflected from the illuminated surface passes into a collector, whereupon it is converted into an electrical signal by an optoelectronic arrangement. The signal is then resolved into alternating and direct current components, and a roughness index is calculated by multiplying a scaling coefficient with the ratio of the alternating to the direct current component.

The importance of illuminating the surface at a relatively low angle is recognised in U.S. Pat. No. 4,019,066. Light striking the surface at a low angle serves to accentuate the contrast between the light and shadows cast by the "landscape" features on the surface. Shadows cast from light striking the surface at other than optimum angles tends to provide less information about the surface when the shadows are analysed. The approach taken in U.S. Pat. No. 4,019,066 to generate 'useful' shadows is to precisely arrange the light source at a particular angle of illumination and to only illuminate a very small area of the surface. The collector also includes an aperture to further limit collected light to that reflected from a surface area of around $\frac{1}{100}$ of a square millimeter.

Precision alignment of the light source to the sheet-surface is cumbersome, and maintaining the angle of illumination can be difficult, particularly when the apparatus is employed in the paper mill environment. Moreover, like air-leak instruments, the apparatus of U.S. Pat. No. 4,019,066 can not readily analyse how the roughness varies across the plane of the sheet.

Therefore, it would be advantageous to provide an apparatus that overcomes these shortcomings of the prior art.

In this specification, where a document, act or item of knowledge is referred to or discussed, this reference or discussion is not an admission that the document, act or item of knowledge or any combination thereof was at the priority date:
(i) part of common general knowledge; or
(ii) known to be relevant to an attempt to solve any problem with which this specification is concerned.

SUMMARY OF THE INVENTION

According to a first aspect of the present invention there is provided a sheet-surface analyser including:
   illuminating means for illuminating the sheet-surface to enable features of the sheet-surface to cast shadows on the sheet-surface;
   capturing means for capturing an image of the shadows;
   analysing means for analysing the captured shadow-image to thereby analyse the sheet-surface; and
   curving means for curving the sheet, wherein the illuminating means and the curving means are configured to enable the illuminating means to illuminate a curved part of the sheet-surface so that features of the sheet-surface cast shadows on the sheet-surface and the capturing means is configured to capture said shadow-image.

Casting shadows on a curved sheet-surface rather than on a flat surface means that angles of illumination giving rise to shadows which encode information about a sheet-surface feature are 'automatically' included in the captured image and analysed, without the need for precision alignment of the illuminating means relative to the sheet-surface. Moreover, capturing a high resolution image gives far more information than measuring a single extremely small spot on the sheet-surface area of a moving web. For example, the image provides spatial information in all directions within the plane of the sheet, instead of just one direction. Also there is no need for the paper to be moving, which simplifies the apparatus for benchtop use.

This also obviates the necessity of using sophisticated and expensive optoelectronic arrangements to analyse the shadows and thus the sheet-surface, which can instead be analysed by fairly standard image analysis software.

The curving means of the present invention may take any convenient form. In a preferred embodiment the curving means is a curved surface around which at least part of the sheet is locatable. The curved surface may for example form part of a cylindrical drum.

A significant benefit of the curved surface is that it facilitates holding the sheet securely in a known position, simply by adding light tension to the sheet via the rubber rollers. If a flat surface were used, then provision would have to be made for vacuum, electrostatic or other mechanisms to hold the sheet securely in place on the surface, thus greatly complicating the apparatus.

The sheet-surface analyser may further include advancing means for advancing the sheet towards and locating the sheet around the curving means. Preferably, the advancing means is at least one roller located relative to the curving means such that a sheet placed between the roller and the curving means is advanced by action of the or each roller towards and around the curving means.

A further advantage of using a curving means along with advancing means is that it facilitates making measurements on a moving web (such as a paper web) at any convenient location where the web is wrapped around the curving means. Flash illumination, or a high speed camera can be used to effectively freeze motion of the web where the optics of the camera are appropriately configured. Such an application could be realised at low speed for laboratory use and at high speed on a paper machine.

Where tension is applied to the paper by the equipment there is no need for

In preferred embodiments, the sheet-surface analyser is a desk-top unit, with the curving means, illuminating means, capturing means and advancing means contained within a casing having an aperture, the arrangement being such that a sheet inserted into the aperture, is advanced towards and around the curving means, analysed and advanced out of the casing.

Preferably, the casing incorporates a display for receiving input parameters related to the sheet-surface analysis and for visually displaying the results of the analysis.

Typically, the analysing means includes:
a processor; and
a computer readable medium storing a computer program which when executed by the processor derives a two-dimensional array of light-intensity values from the captured shadow-image and calculates a sheet-surface value from the array, wherein in calculating the sheet-surface value a selected region of the array is weighted to contribute more to the sheet-surface value than the remainder of the array.

Preferably, the two-dimensional array is represented by a matrix of rows and columns of light-intensity values, and wherein deviation values of respective rows and columns are calculated, the deviation value being a measure of the average deviation (such as the standard deviation) of the light-intensity values in that row or column from the mean value in that row or column and wherein said selected region includes one row and/or column of the matrix having a maximum deviation value, such that the light-intensity values in said row and/or column are more heavily weighted in calculating a sheet-surface value.

The inventors have found that matrix rows and/columns having a high standard deviation of the elements from the mean light intensity value for that row or column tend to provide more information about sheet-surface properties than those having low standard deviation. Therefore, the selected region is preferably at least one matrix row and/or column where the standard deviation of the row or column is greater than the standard deviation for at least one other row or column.

The sheet-surface value may be calculated from a weighted sum of standard deviation calculated for each row and/or column, the weight for each row and/or column being in proportion to the standard deviation for that row or column, wherein each row or column contributes to the sheet-surface value in proportion to its standard deviation.

Weighting the data in this way, or similar is advantageous but not essential.

The sheet-surface value may be the mean of:
the mean of the weighted standard deviation calculated for each matrix row; and
the mean of the weighted standard deviation values calculated for each matrix column.

The computer program may also includes means for correcting the captured image for non-uniformity of illumination before calculating the sheet-surface value. In preferred embodiments, the means is computer program code for best fitting a low-order polynomial to the elements of each matrix row and subtracting each element from the value of the fitted polynomial at that element.

The sheet-surface analyser of the present invention may analyse a variety of surface properties. The sheet-surface value may for example represent the roughness of the sheet.

According to a second aspect of the present invention there is provided a method of analysing a sheet-surface, including the steps of:
curving the sheet;
illuminating the surface of the curved sheet to enable features of the sheet-surface to cast shadows on the surface of the curved sheet;
capturing an image of the shadows; and
analysing the captured shadow-image.

Preferably, the method includes the steps of:
progressively advancing the sheet over a curved surface; and
capturing an image of the shadows cast on the sheet surface at predetermined intervals.

A method according to claim 16 wherein the step of analysing the captured image includes the steps of:
deriving a two-dimensional array of light-intensity values from the captured shadow-image; and
calculating a sheet-surface value from the array, wherein in calculating the sheet-surface value a selected region of the array is weighted to contribute more to the sheet-surface value than the remainder of the array.

Preferably, the two-dimensional array is represented by a matrix of rows and columns of light-intensity values, and wherein deviation values of respective rows and columns are calculated, the deviation value being a measure (such as the standard deviation) of the average deviation of the light-intensity values in that row or column from the mean value in that row or column, and wherein said selected region includes one row and/or column of the matrix having a maximum deviation value, such that the light-intensity values in said row and/or column are more heavily weighted in calculating a sheet-surface value The step of calculating a sheet-surface value may include the steps of:
  calculating the deviation value for each matrix row and/or column;
  multiplying each deviation value by a weight that is in proportion to the deviation value; and
  averaging the weighted deviation values to calculate the sheet-surface value, wherein each row or column contributes to the sheet-surface value in proportion to its deviation value.

The method may include the further step of averaging the average weighted deviation value for the matrix rows and the average weighted deviation value for the matrix columns to thereby calculate the sheet-surface value.

Preferably, the method may further include the step of correcting the matrix for non-uniform illumination before calculating the sheet-surface value. The step of correcting the matrix includes the steps of:
  best fitting a low-order polynomial to the elements of each row of the matrix; and
  subtracting from each element the value of the best-fitted polynomial at that element.

BRIEF DESCRIPTION OF THE DRAWINGS

A preferred embodiment of the present invention will now be described with reference to the accompanying drawings. In the drawings:

FIGS. 16 and 17 are screen shots of sheet-surface analysis displayed on the touch-screen.

DETAILED DESCRIPTION OF THE DRAWINGS

Figure 1:
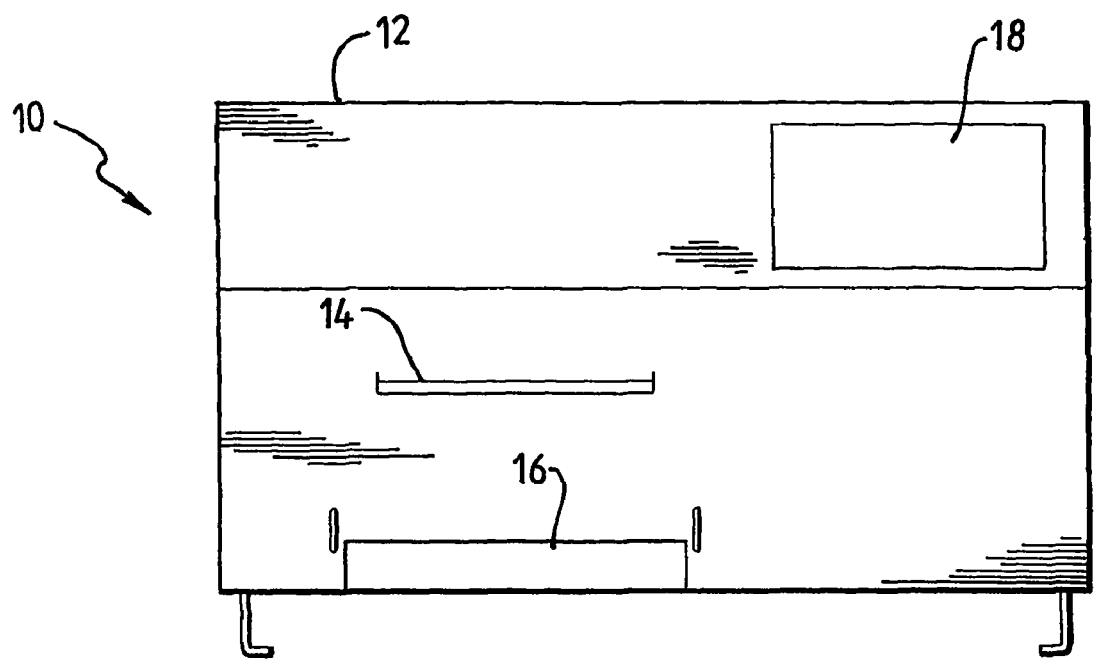
FIG. 1 is a front elevation view of a sheet-surface analyser in accordance with the present invention.
Figure 2:
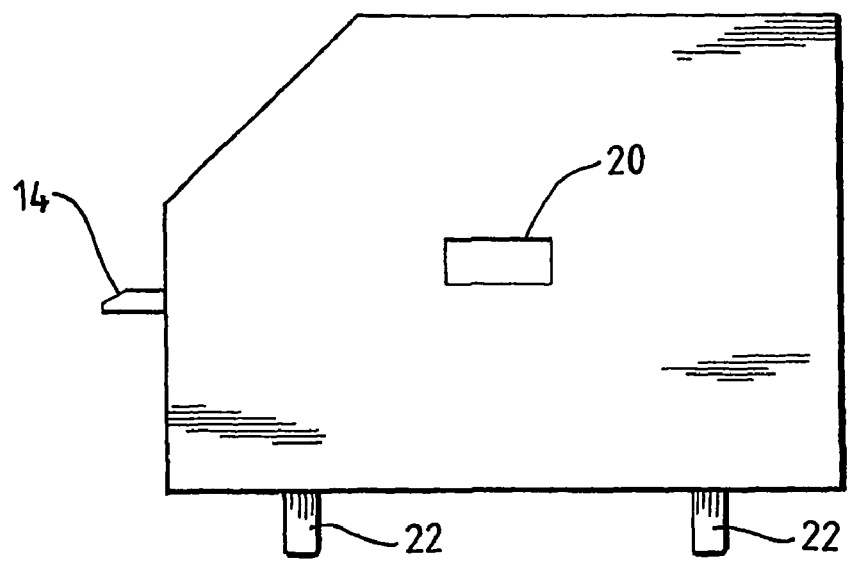
FIG. 2 is a side elevation view of the apparatus illustrated in FIG. 1.
Figure 4:
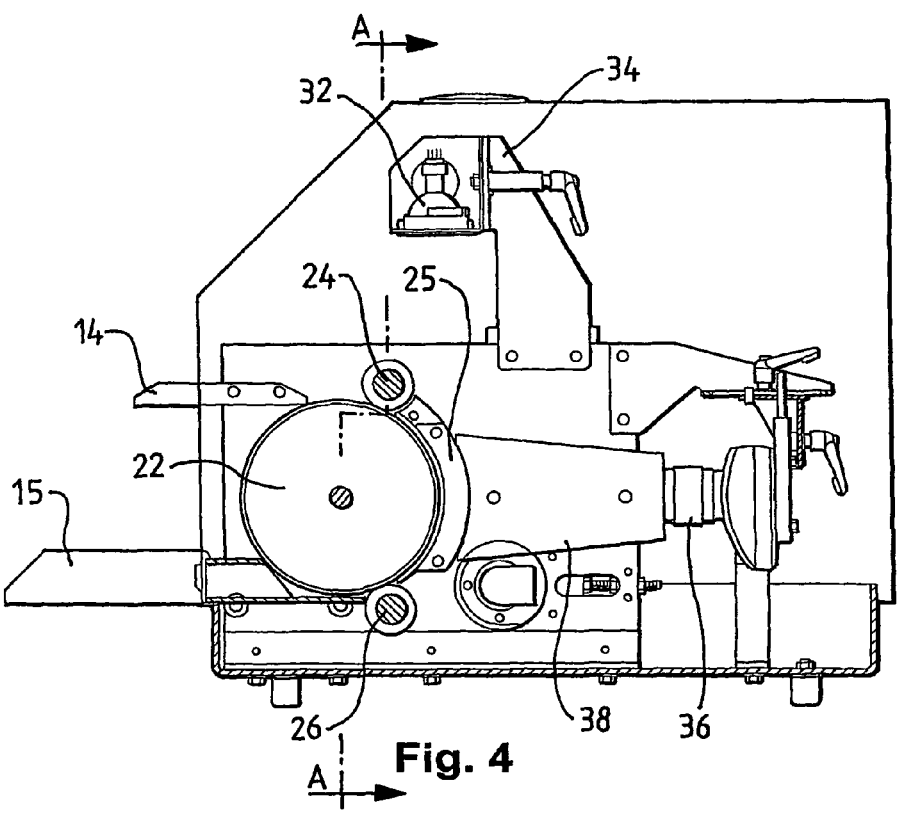
FIG. 4 is a cross-sectional view of the apparatus through the line B-B in FIG. 3.

FIGS. 1 and 2, show a sheet-surface analyser 10. The components of the analyser are housed in a metallic opaque casing 12. that includes legs 22 to allow the analyser to be set on a workbench in a paper mill to analyse paper sheets in the course of production. The casing has a longitudinally extending lip 14 that serves as an input tray for the paper sheet being analysed. The length of the input tray 14 is such that a cross-deckle strip (being a piece of paper collected from a paper machine reel that covers the whole width of the machine) may be fed into the analyser 10 and analysed. A section 16 is also removed from the lower edge of the casing's front face, to serve as an outlet for the sheet after it has been analysed. As illustrated in FIG. 4, an external output tray 15 is affixed to the casing 10 over the removed section 16 to conveniently guide the sheet out of the analyser.

Figure 3:
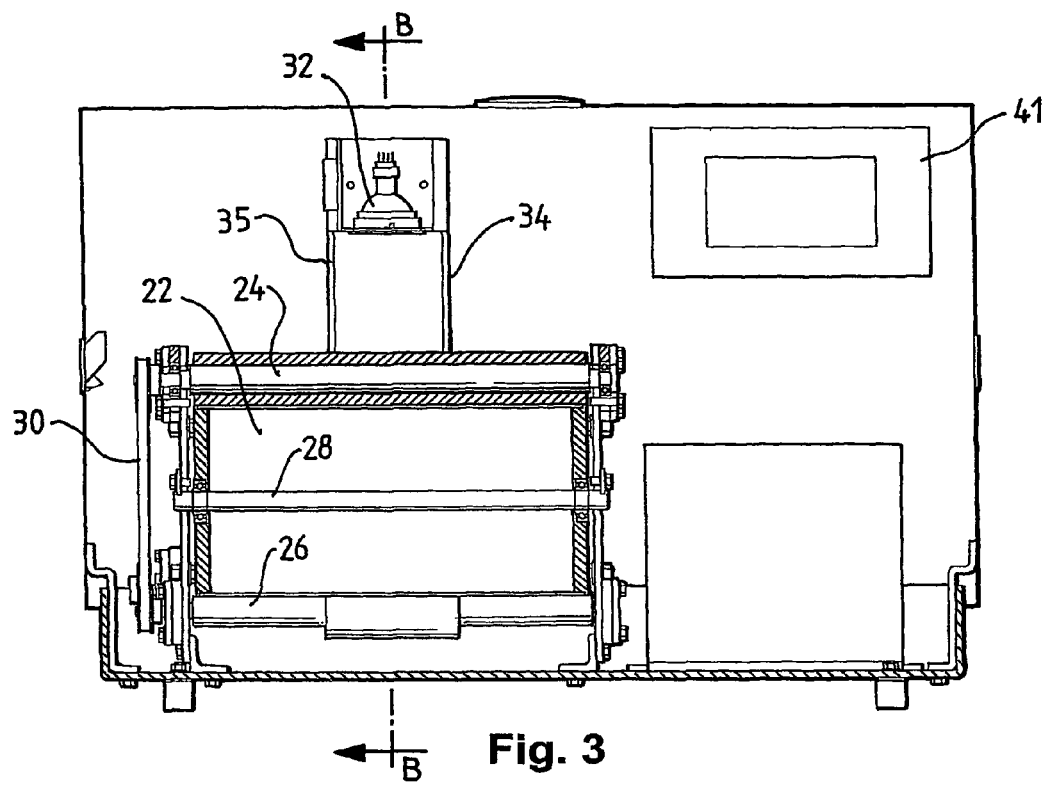
FIG. 3 is a plan view, partly in cross-section through the line A-A in FIG. 1, illustrating the internal components of the apparatus.

Turning to FIGS. 3 and 4, a roller assembly comprising a cylindrical drum 22 and an upper 24 and lower 26 roller is located towards the front end of the casing. The axes of the upper and lower rollers 24 and 26 and the cylindrical drum 22 are parallel. The cylindrical drum 22 is fixably mounted within the casing on an axle 28 and is manufactured from a metallic or other hard material. The upper 24 and lower rollers 26 are soft relative to the drum 22 and are manufactured from a rubber-based or similar material A light source 32 is located above the roller and is connected within the housing via a pair of mounting plates 34 & 35. A digital camera 36 is located to face approximately normal to the curved surface of the roller 22. A touch screen 42 is located on the upper edge of the casing 12. A computer processor and memory 40 are also housed within the casing 12.

Figure 5:
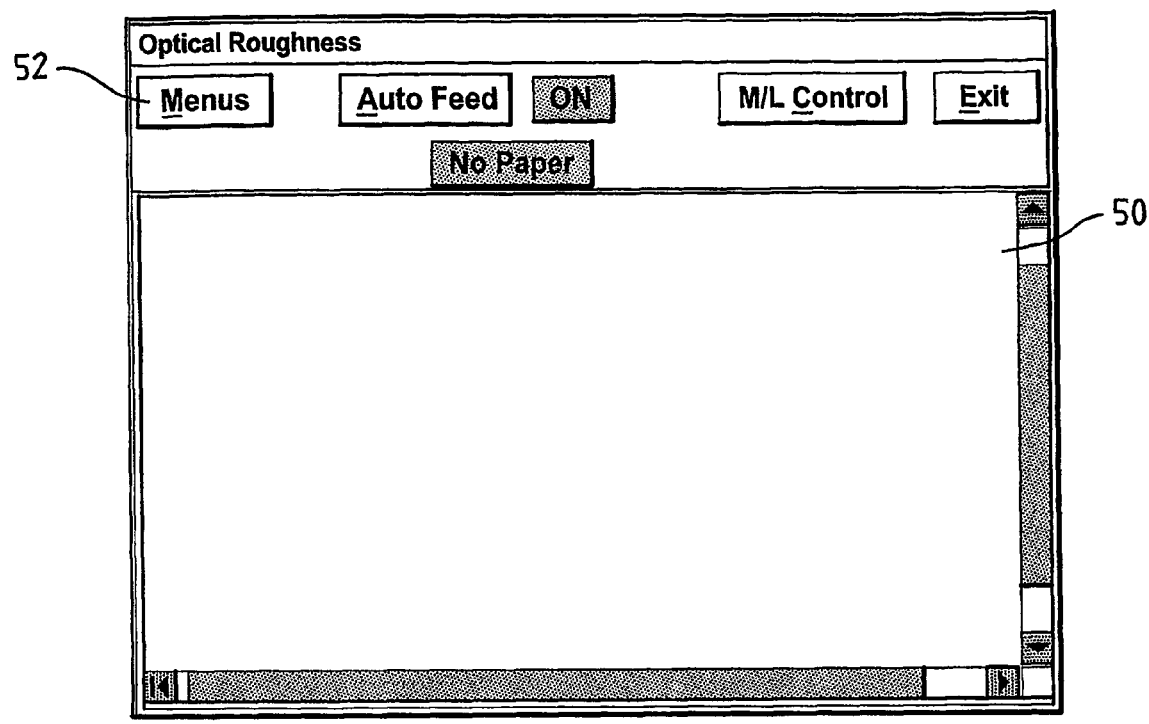
FIGS. 5 to 9 are screen shots of the user interface to the sheet-surface analyser that is displayed on the touch-screen.

To analyse a sheet such as a sheet of paper, an operator first selects the 'Menus' button 55 (FIG. 5) that is displayed on the tough screen 42 as part of the main window 50. Display of the user interface on the touch screen and the acceptance and processing of operator-commands is controlled by a computer program stored in the memory 40 and executed by the processor, as understood by those skilled in the art. A control program for operating the various components of the analyer is also stored in the memory for execution by the processor.

Figure 6:
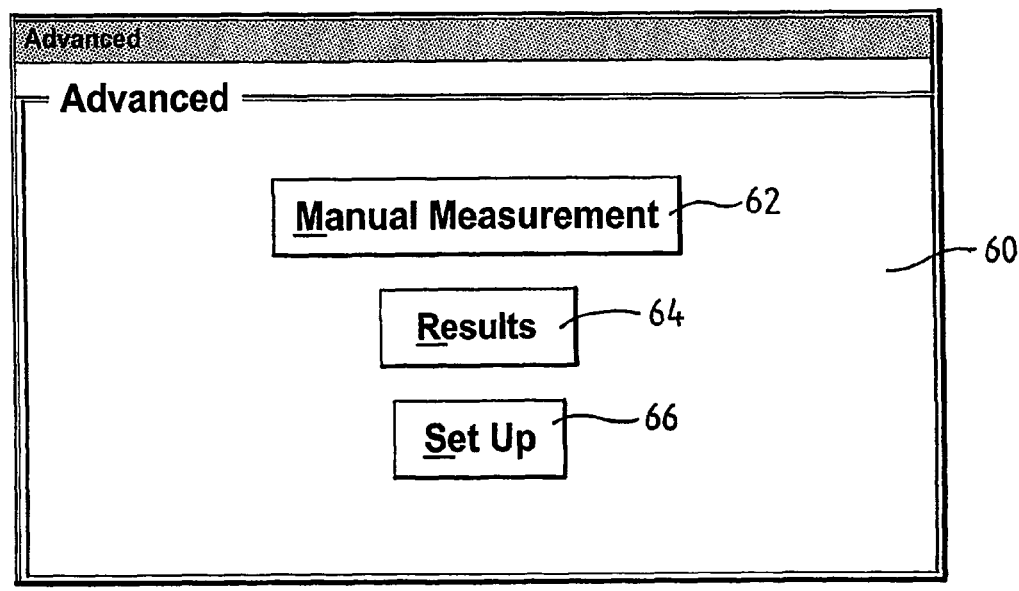
Figure 7:
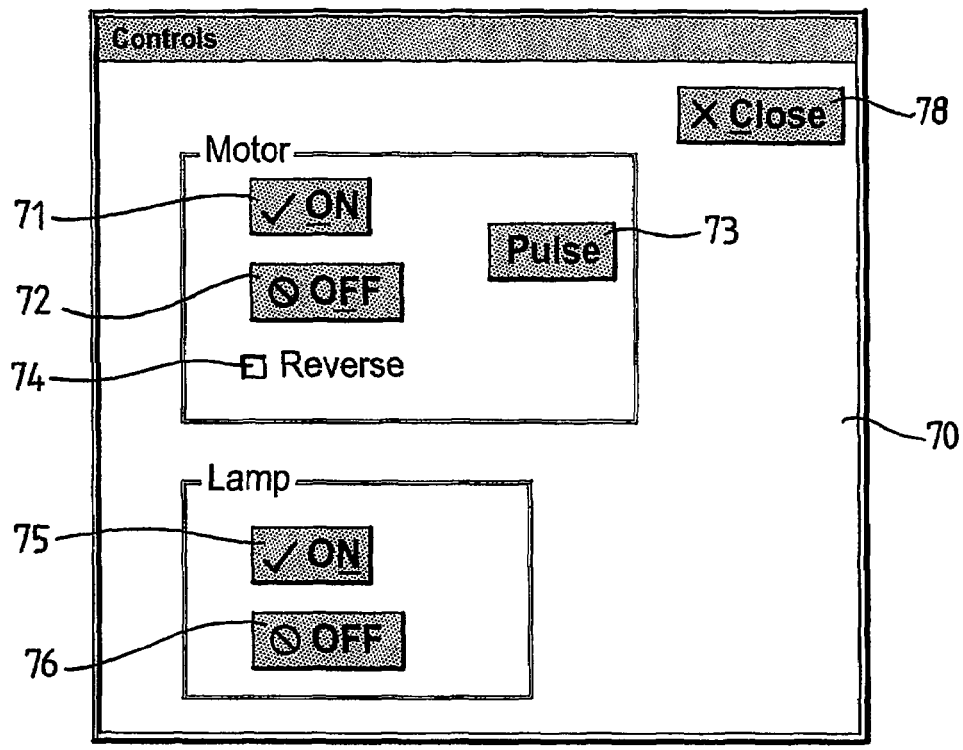

The 'Menus' button displays a window 60 (FIG. 6) that enables the operator to either select Manual Measurement 62, Set Up 66 certain parameters for Automatic Measurement, or display the Results 64 of an earlier sheet-surface analysis. Where Manual measurement is selected (FIG. 7), a window 70 is displayed on the touch-screen allowing the operator to manually switch the roller assembly On 71 and Off 72, as well as into a Pulsing mode 73. The roller assembly 24, 26 may also be placed into reverse by selecting the checkbox 74. Similarly, the light-source 32 may be manually switched On 75 and Off 76 by the buttons on the touch screen. The window 70 is closed by selecting the Close button 78 which returns the operator to the Menus screen 60.

Figure 8:
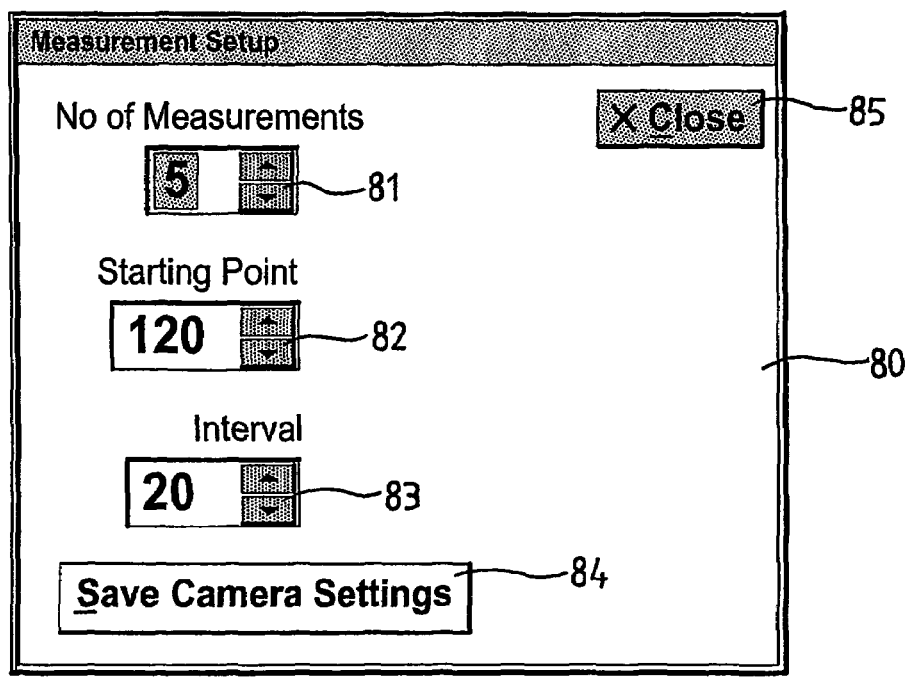

Selecting 'Set Up' 66 displays a window 80-(FIG. 8) on the touch-screen 42 that allows the operator to enter parameters related to the automatic analysis of a sheet-surface. These parameters are the Number of measurements 81 taken of the sheet-surface, the Starting point 82 on the sheet from which the measurements are taken, and the Interval 83 between each measurement. As described in further detail below, a measurement of the sheet-surface is taken by illuminating the sheet-surface and photographing the illuminated surface with the digital camera 36. The entered parameters may be saved to analyse later sheets, by clicking the Save button 84. The window 80 is dosed by clicking Close button 85, returning the operator to the Menus screen 60.

Figure 9:
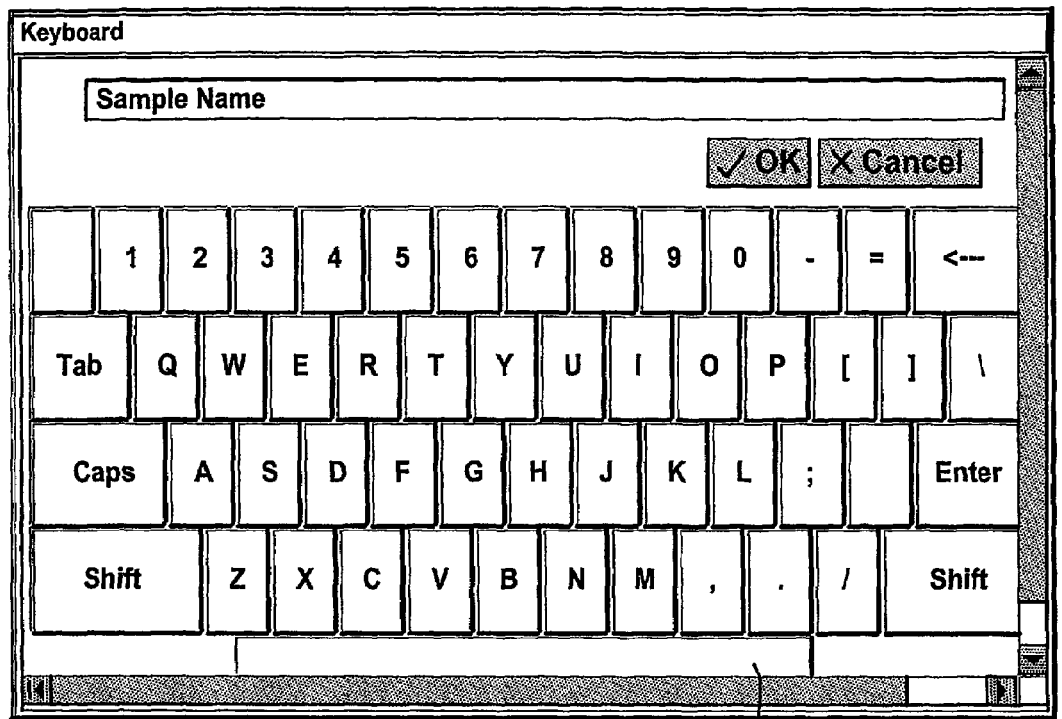

Once the parameters are entered, the sheet is fed into the analyser 10 through the input tray 14 and the leading edge of the sheet is located between the upper roller 24 and the drum 22. A sensor (not shown) senses the sheet and forwards an electronic signal to the computer processor 40 which then displays a window 90 (FIG. 9) on the touch-screen, allowing the operator to enter a name for the sample against which the analysis results may be saved.

After the name is entered, the computer program sends a control signal to the upper roller 24 causing it to rotate and feed the sheet around the curved surface of the drum 22 to the measurement starting point entered by the operator. The sheet is held onto the surface of the drum 22 and guided towards the lower roller 24 by a pair of guide plates 25 provided on each edge of the drum 22. A second sensor (not shown) senses when the edge of the sheet passes between the lower roller 26.

The control program then causes the light source 32 to shine on the sheet-surface to thereby cast a series of shadows and the camera to photograph the illuminated surface. The sheet is then advanced by the roller assembly 24, 26 and photographed at the specified intervals entered by the operator. An example of a photographed (ie captured) image is given in FIG. 10.

Casting shadows on the surface of a curved sheet (such as that provided by the cylindrical drum 22), rather than a flat sheet as in the prior art is advantageous for analysis of a surface property, such as roughness, as outlined below. The principles underlying casting shadows on a curved sheet in order to analyse a surface property are illustrated by reference to FIGS. 10 and 11. Beams of light emanating from the light source 32 strike the sheet-surface at a plurality of angles of illumination. Towards the top 40 of the illuminated region, the angle of illumination is closer to the normal to the surface, with the result that less pronounced shadows are cast in this region. This is analogous to no shadows being cast at noon As the sheet curves around towards the bottom 42 of the illuminated region, the angle of illumination becomes smaller and consequently longer shadows are cast by minor 'landscape features' of the surface such as those due to surface roughness. Again, this is analogous to long shadows cast at sunrise or sunset.

The simultaneous casting of shadows of different lengths by beams of light striking the surface at varying angles of illumination may be further exploited by the weighting functions of the image analysis program referred to in more detail below. Essentially, it has been found that shadow regions of better resolution, generally occur towards the centre of the illuminated region. Accordingly, these shadows have a greater effect in the analysis than those cast at the periphery of the illuminated region.

The inherent sensitivity from different angles of illumination may also be used to adjust the overall sensitivity of the analyser, so that it may be used across a wide variety of paper sheets. For example, whilst in general, the camera is positioned roughly in line with lower edge of the illuminated region (as illustrated in FIG. 2), the camera may also be raised towards the upper edge where shorter shadows are cast to thereby reduce the sensitivity of the analyser.

The range of angles can also be altered by changing the camera-to-drum distance and/or the light-source-to-roll distance and by changing the field of view through use of a different lens for a given camera. Each of these will change the sensitivity of the analyser and the flexibility of the design allows a trade off between sensitivity and compactness.

In addition, the roller assembly 24,26 allows the angles of illumination (and correspondingly the relationship between shadow lengths and surface topography) to be known and monitored for calibration purposes. The determination, on the acquired image, of the position of the edge, between light and dark, provides a reference delineating boundary because at this boundary, the angle of incidence of rays from the illuminating source strike the sheet-surface tangentially. With knowledge of the geometry of the instrument (roller diameter, camera to sheet distance, camera and lens specifications and light source distance from the roller) the range of angles of illumination can be calculated and used to calibrate the analyser.

After the image of the shadows is captured by the camera, a computer program analyses the image to thereby analyse the sheet-surface itself. A two dimensional matrix is derived from the image, with the elements of the matrix representing the light intensity at each pixel of the image. The next step in the analysis is to remove a 'slowly varying component' from each row of intensity values. This component is thought to be due to non-uniform illumination from the light source and/or vignetting from the camera.

Figure 12:
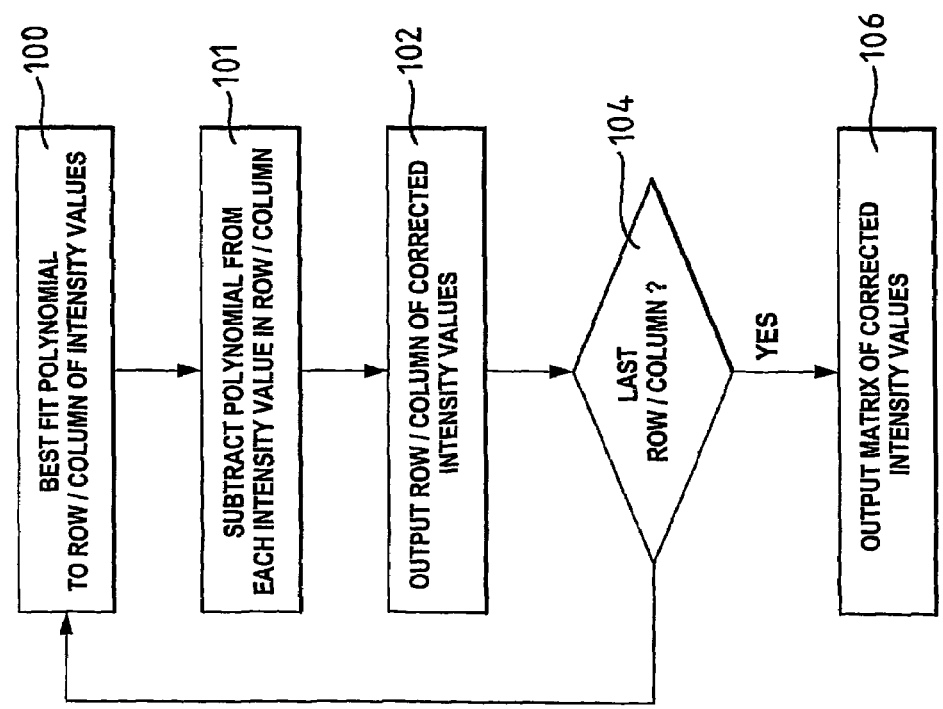
FIG. 12 is a flow chart of the algorithm for correcting the image for non-uniform illumination.

Turning to FIG. 12, the slowly varying component is removed from a row by best fitting a low order polynomial, such as a Chebyshev polynomial to the row 100. The best-fit polynomial is then subtracted from each element of the row to yield a row of corrected intensity values 102. A test is performed at step 104 of whether the current row is the last row of the matrix. A matrix of corrected intensity values is output at step 106 when the last row is reached, or the process returns to step 100 to remove the slowly varying component from the next row, as the case may be.

The slowly varying component may be removed from the row of intensity values by other techniques such as applying Fourier high pass filtering or a wavelet based high pass filtering. The horizontal and vertical Fourier Transforms also provide information about the roughness at different scales and can be used to locate peaks due to wiremarks, couch marks, felt marks, or any other periodic structure in the sheet. The strength of the peaks may be measured to provide information about the extent to which the periodic structures contribute to the overall roughness of the sample.

Figure 13:
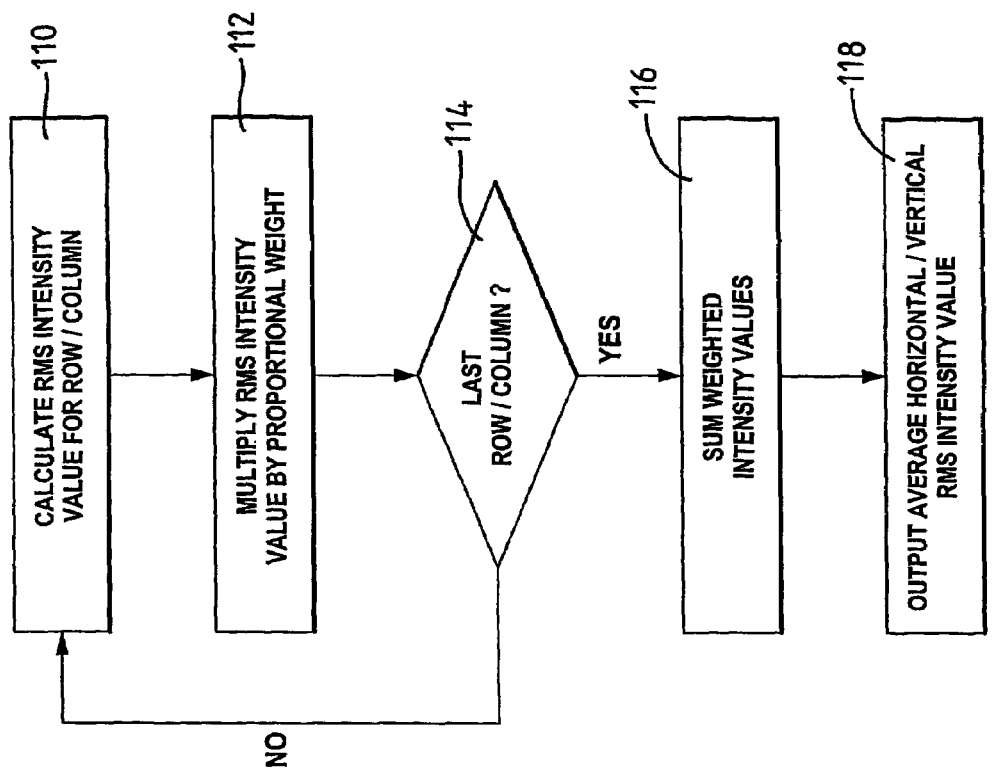
FIG. 13 is a flow chart of the algorithm for calculating a roughness value of the sheet.

Turning to FIG. 13, the matrix of corrected intensity values is analysed statistically to calculate a sheet-surface value for the particular sheet-surface property being analysed. In the case of roughness, the sheet-surface value is interpreted as a roughness index for the sheet-surface.

At step 110, the root-mean-square (RMS) intensity value for a row is calculated by applying the formula:

$$x_{\text{rms}} = \sqrt{\frac{1}{N}\sum_{i=1}^{N} x_i^2}$$

Where $x_{rms}$ is the RMS intensity value for a row and $x_i$ is the difference between the intensity value at a particular pixel i in the row and the mean intensity value for the row and N is the number of pixels in the row.

Figure 10:
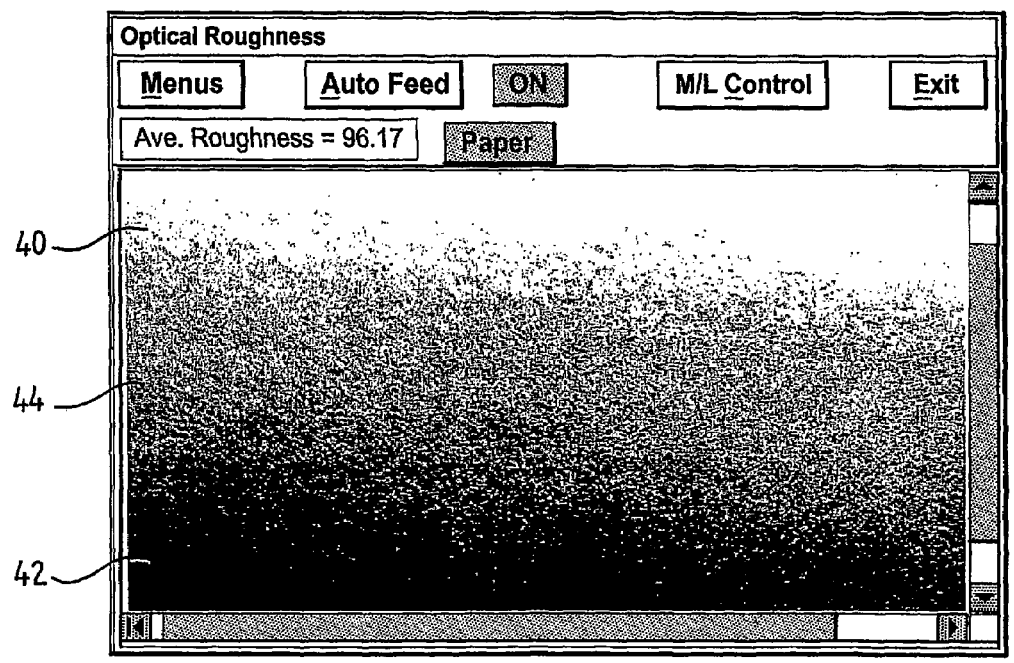
FIG. 10 is an illustration of a captured image of shadows cast on the sheet-surface of the curved sheet by the illuminating means.
Figure 11:
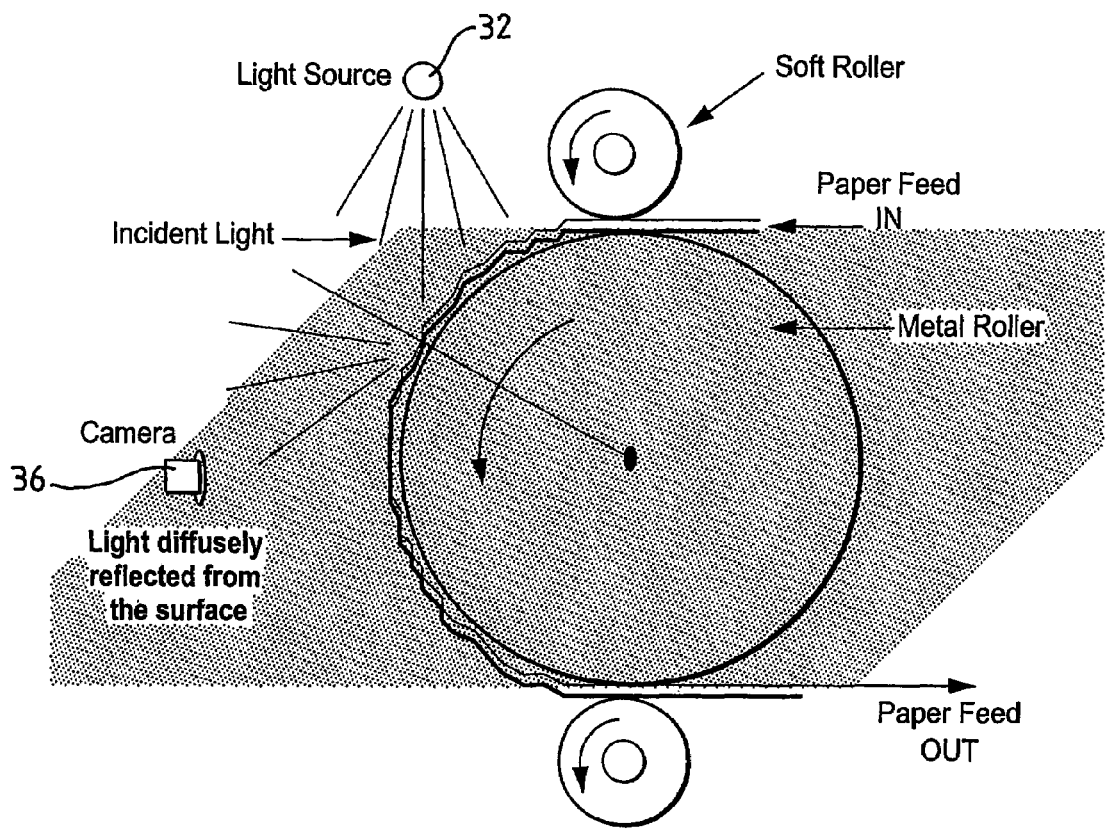
FIG. 11 is a schematic diagram illustrating the principles of the present invention.
Figure 14:
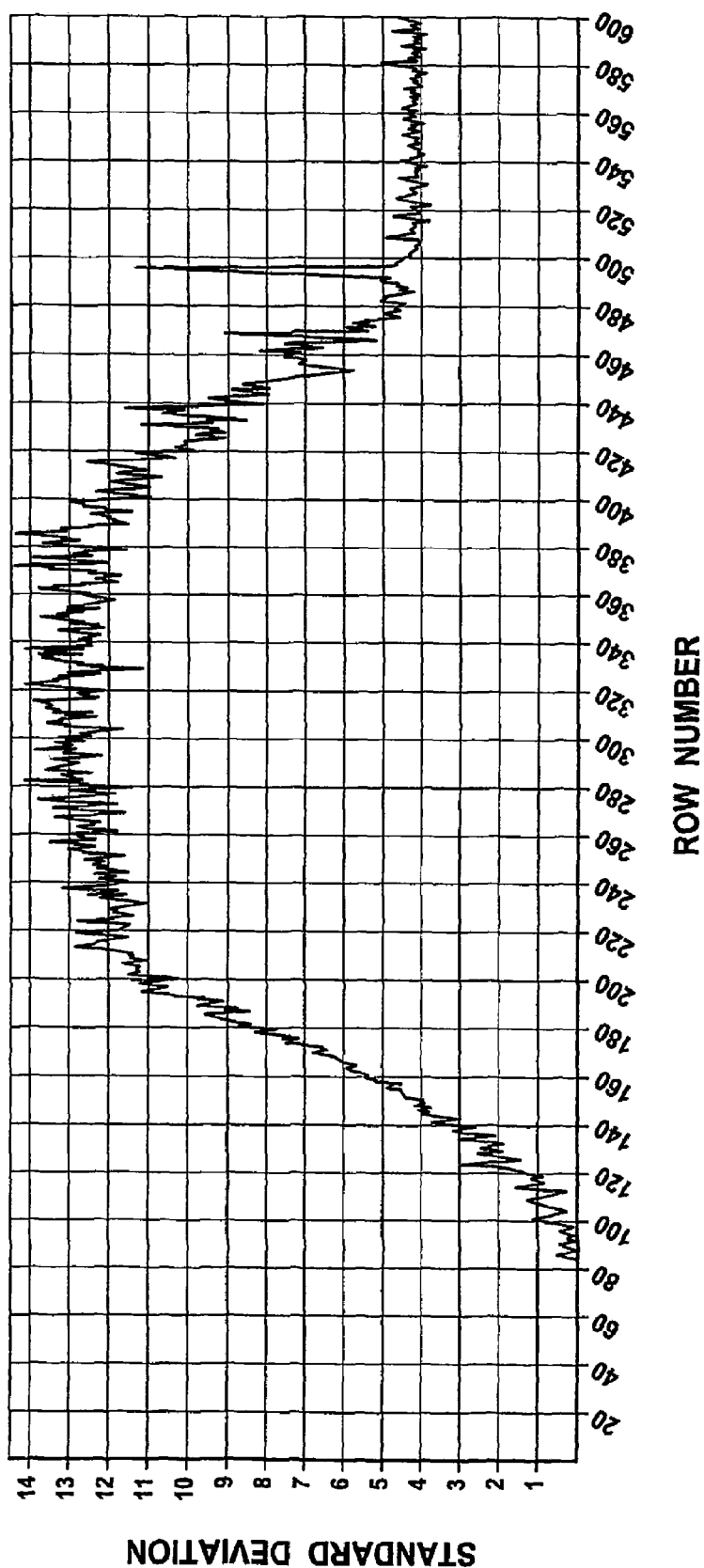
FIGS. 14 and 15 are graphs that respectively illustrate how variation in shadow distribution is maximal towards the centre of the image and the roughly linear decay in light intensity across the curvature of the sheet.
Figure 15:
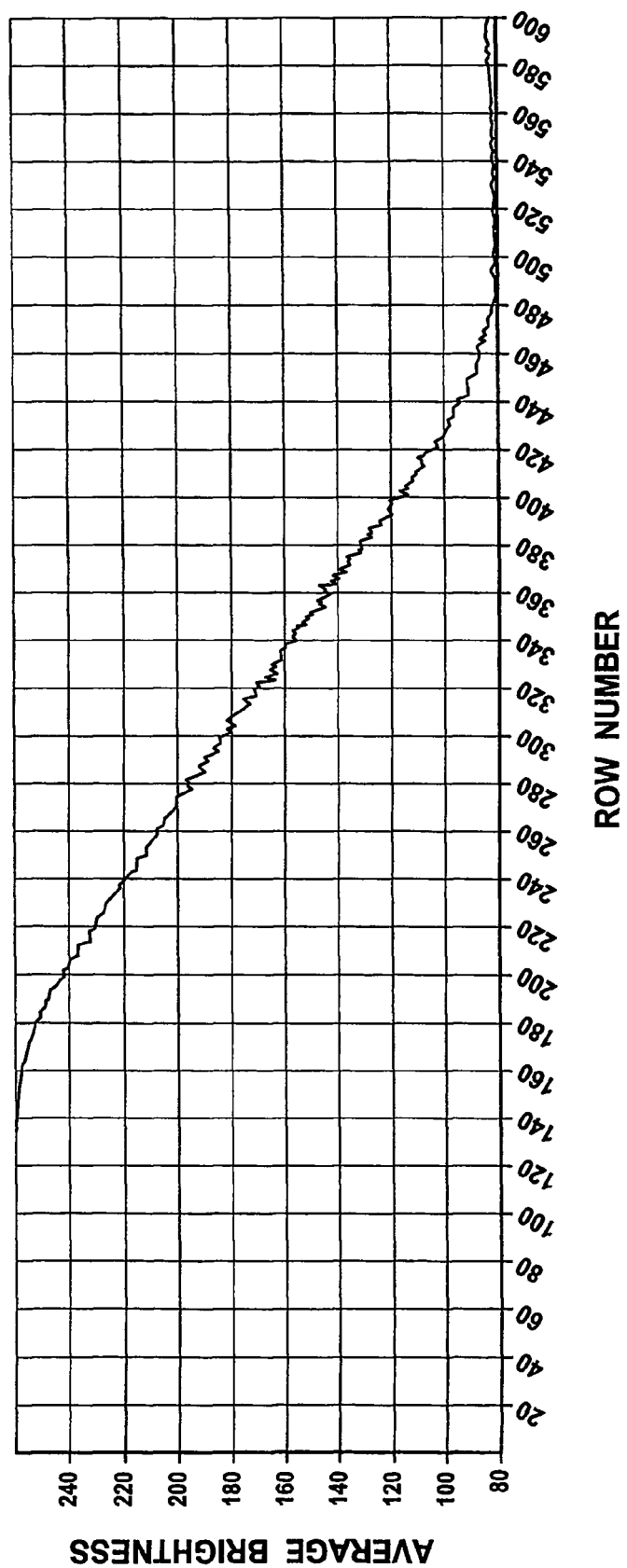

At step 112, the RMS value for the row is multiplied by a weight value that is proportional to the RMS value for that row. Weighting rows in proportion to the RMS value ensures that shadows located towards the centre of the image contribute more in the calculation of the roughness index than shadows on the periphery. This is explained by turning briefly to the graph on FIG. 14, which shows that the standard deviation (ie $x_{rms}$ is the above formula) is maximal from between about rows 200 and 400. This of course coincides with the central rows of the image and confirms that weighting the rows in proportion to the RMS value for that row increases the contribution of the higher resolution central shadows to the roughness index. The actual intensity (or 'brightness') values decrease in a roughly linear fashion over the curved surface from top to bottom, as illustrated in FIGS. 10 and 14.

The higher resolution of the central shadows is a result of the low angle of illumination between the light source and the sheet-surface at the central region when the sheet is curved. Moreover, rows at the top of the image tend to be over-exposed (giving zero or low values RMS), and rows at the bottom tend to be under-exposed (also giving low RMS).

Returning to FIG. 13, a test is performed at step 114 on whether the last row has been reached. When it has, the weighted RMS intensity values for each row are summed at step 116 and averaged at step 116 to yield at step 118, an average horizontal RMS intensity value.

Each column of the matrix of intensity value analysed in a similar fashion to the rows, either sequentially or in parallel, to yield an average vertical RMS value.

The roughness index is then calculated from the average of the horizontal RMS intensity value and the vertical RMS intensity value. The process of image-capture and analysis is repeated for point on the sheet specified by the operator and the results are displayed in a window 120 on the touch screen as illustrated in FIG. 122. The results of the analysis may also be exported to a spreadsheet program also running on the computer processor simply by pressing the 'Excel' button 122 (FIG. 17).

In the case of paper sheets, if the manufacturing machine direction (MD), cross direction (CD) and the direction of the path the sheet through the analyser (with respect to the MD and CD directions) are known, then the horizontal and vertical RMS intensity values provide a gauge of the roughness in the MD and CD directions.

Seven samples having wide range of surface roughness were selected from three separate paper mills ranging from very smooth double coated (Impress) to very rough textured (Threads) grades. The optical roughness of each of these samples was measured on the top and bottom sides of the sheet. Table 1 shows the results obtained from an average of seven measurements on each side of the sample.

TABLE 1

Optical surface roughness measured from 7 samples

| Sample | Average optical roughness (Top) | Average optical roughness (Bottom) |
|---|---|---|
| Impress | 51.5 | 52.2 |
| Thermal Base | 65.8 | 67.3 |
| Saxton Smooth | 63.0 | 70.6 |
| Saxton Vellum | 80.0 | 85.6 |
| Glopaque Plus | 88.4 | 92.6 |
| Tudor RP | 105.3 | 97.8 |
| Threads | 118.2 | 123.7 |

These results were compared with air leak roughness measurements such as Bendtsen and PPS, the main parameters of liquid penetration technique "Emtec" PDA and varnishability (an oil drop is spread on the surface of the paper and then measures the length of the stain spread on the surface).

Figure 18:
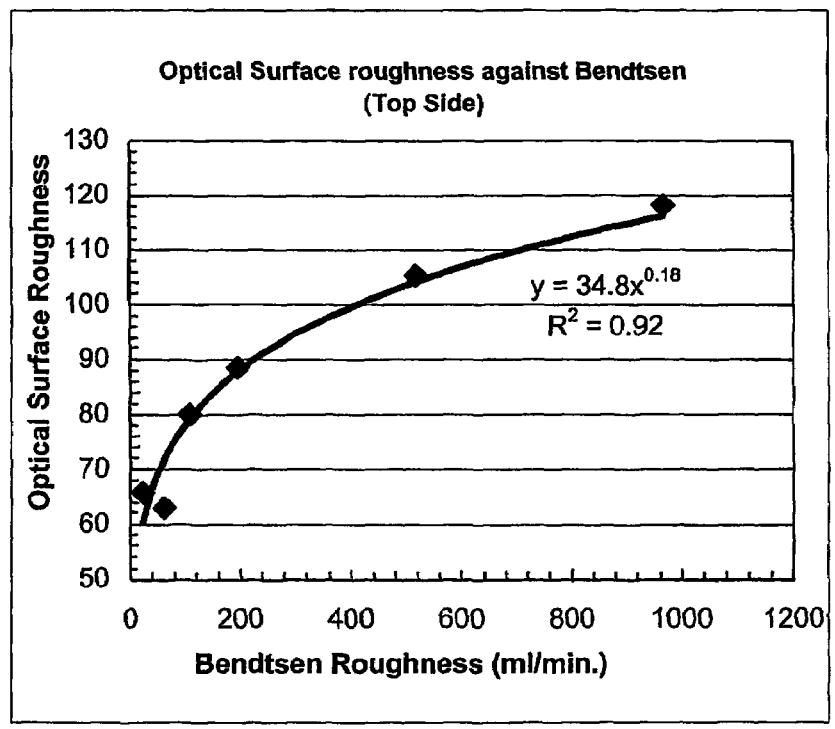
FIGS. 18 to 25 are graphs comparing sheet-surface analysis using the invention and using prior art apparatus and methods.
Figure 19:
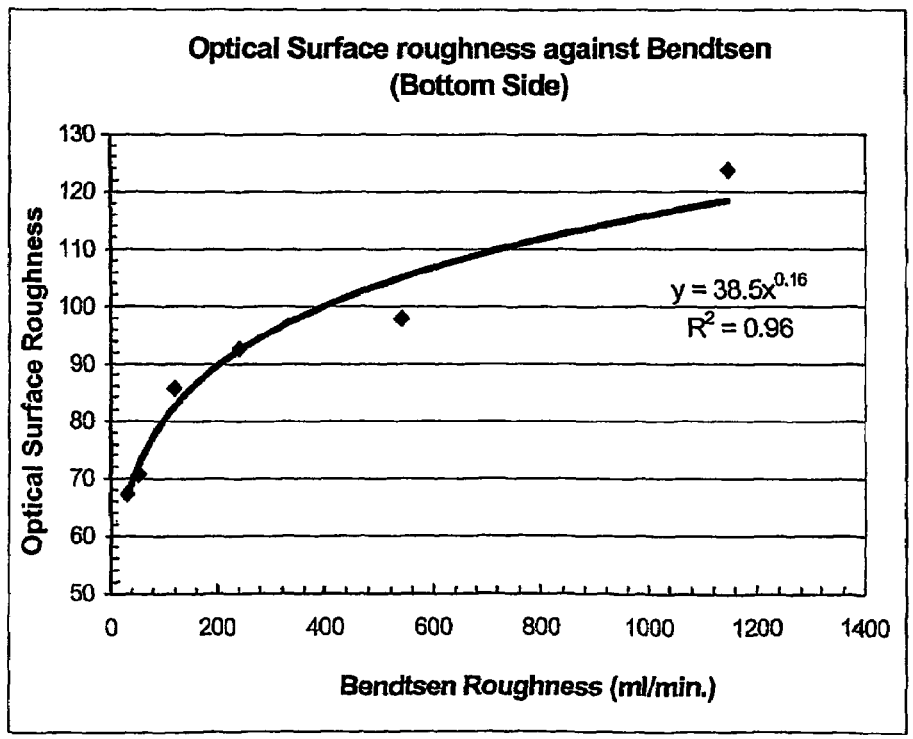

FIGS. 18 and 19 shows the plots of optical roughness against Bendtsen measurements for (a) top and (b) bottom of six samples. An excellent correlation was observed between optical roughness and the Bendsten with R2=0.92 and 0.96 for top and bottom respectively.

Figure 20:
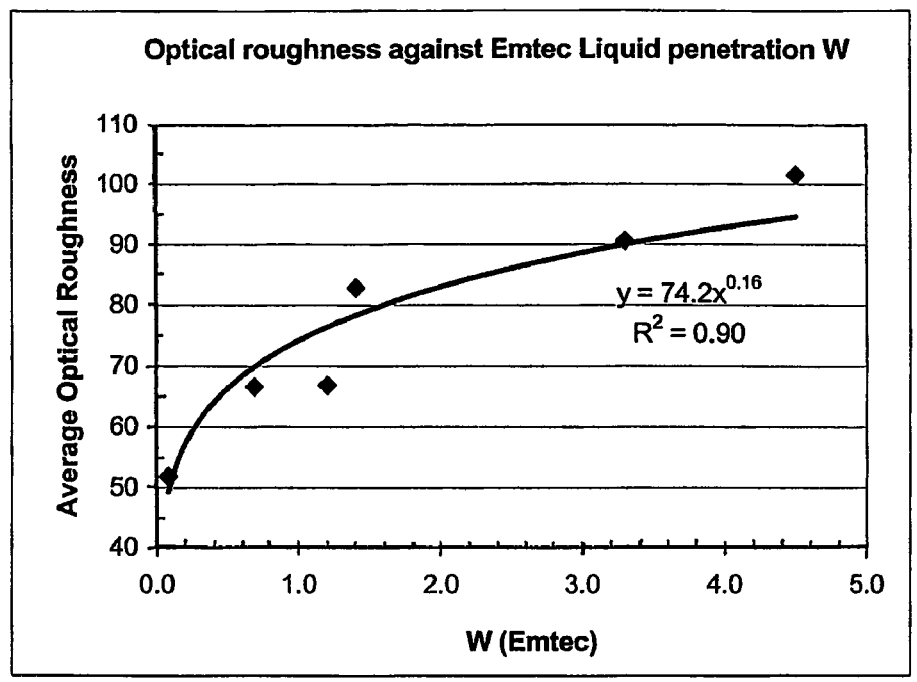

The PPS and "Emtek" liquid penetration measurements were correlated against the average values obtained from top and bottom surfaces. The PPS showed an excellent correlation with optical roughness as shown in FIG. 20.

Figure 21:
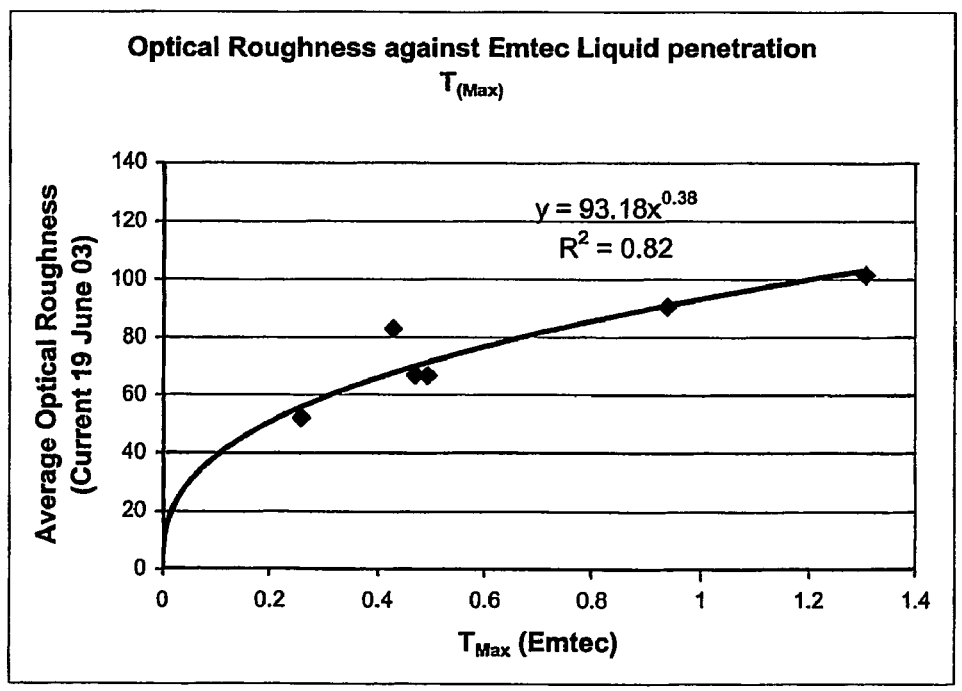
Figure 22:
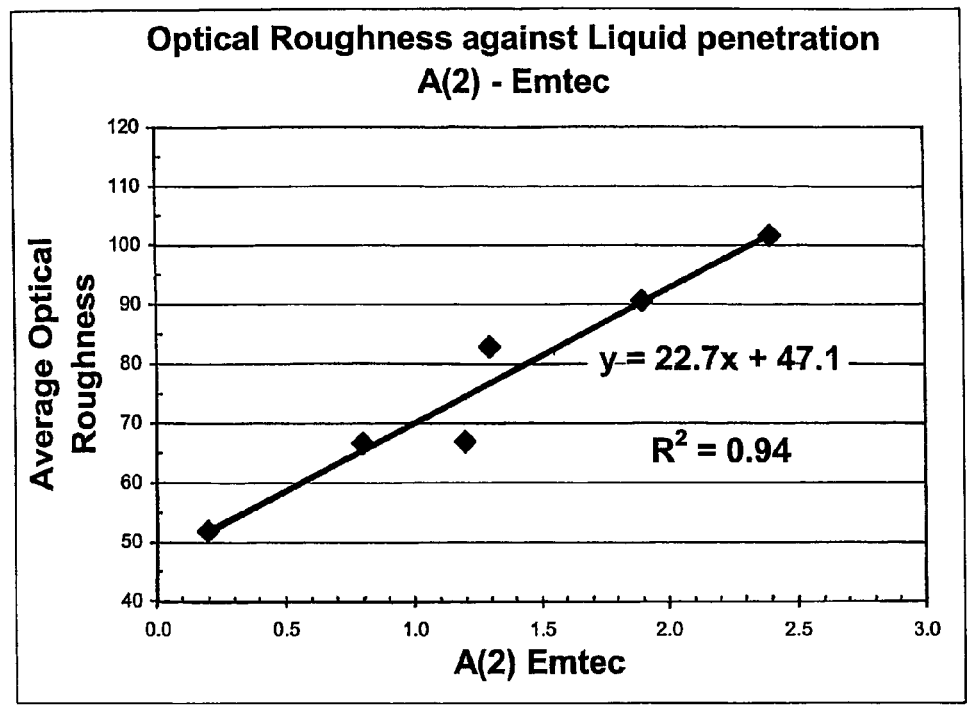
Figure 23:
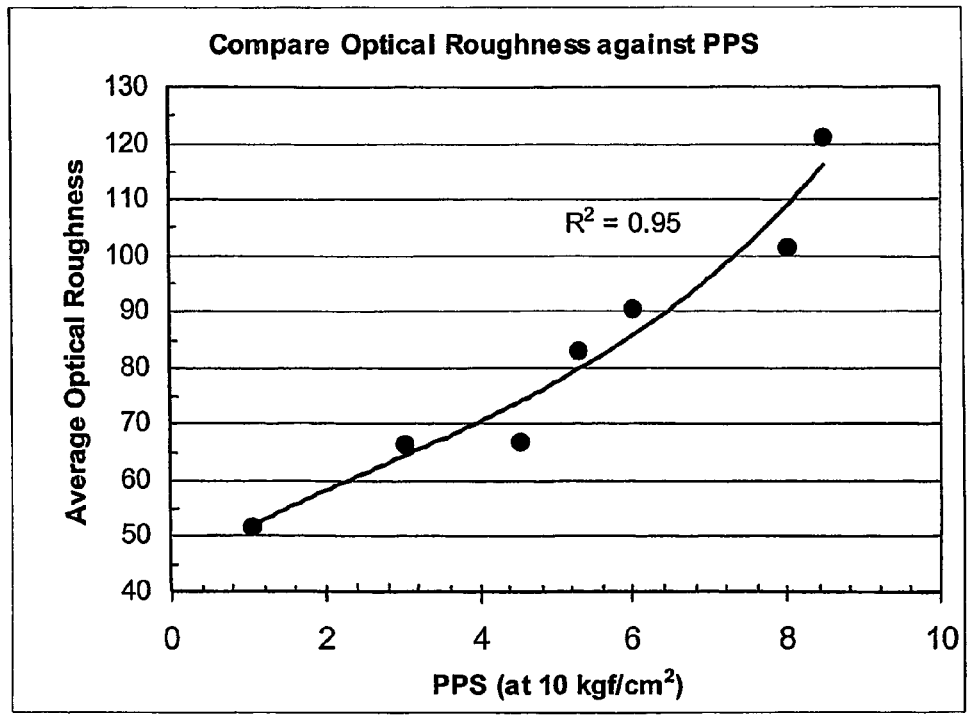

W, Tmax and A(2) are the main parameters obtained from "Emtec" liquid penetration measurement. W is the wettability, which in turns is affected by porosity, roughness and surface sizing. T max is related to surface sizing while A(2) is a combination of the above plus internal sizing of the sheet. Once gain good correlations between these parameters and the optical roughness can be seen in FIGS. 20, 21 & 22. It will be noted that sheet-surface analyser of the present invention is capable of measuring roughness accurately over a wide range of grades between 40 and 120.

Figure 24:
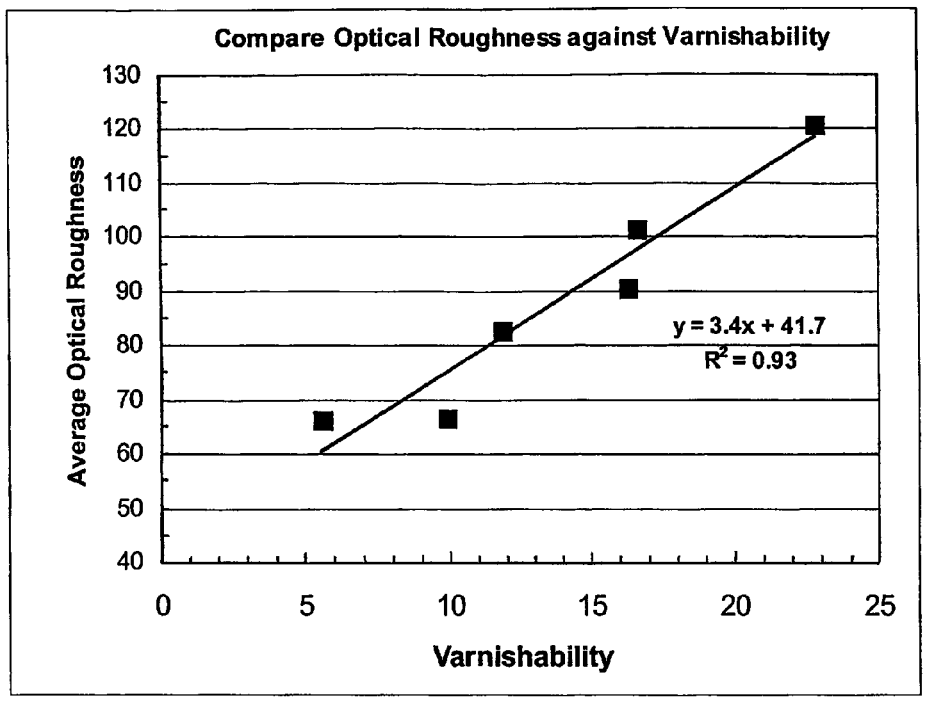
Figure 25:
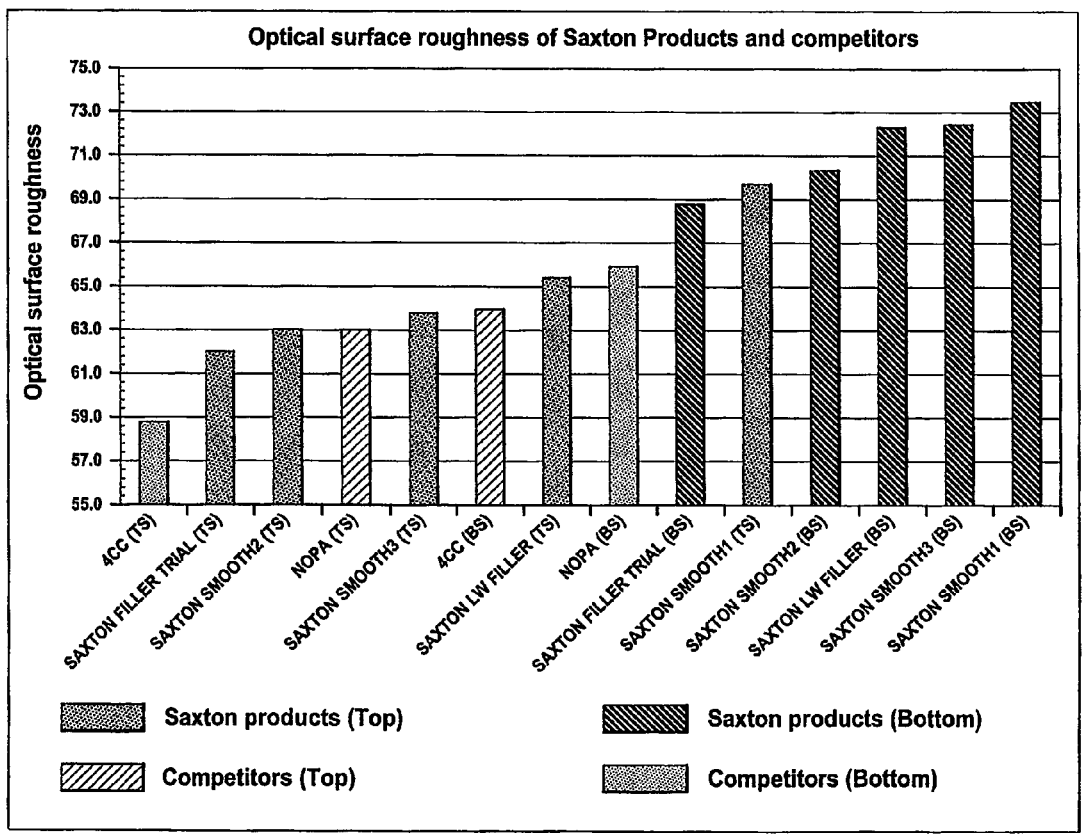

Sensitivity to detect smaller differences within the same grade was also tested. A number of Saxton Smooth makings and two imported competitors were measured. FIG. 24 shows roughness variation between different makings of Saxton smooth (1, 2 & 3). Difference between the two sides of the sheet was also obvious ie. roughness of the bottom sides are always higher than the top side (due to fines being retained more on the top side). The smoothest surface appeared to be the top-side of imported 4CC, followed by the recently run Saxton filler trial (TS).

The above description of the sheet-surface analyser has been by way of a preferred embodiment and numerous variations are possible. For example, whilst the means for curving the sheet is a cylindrical drum it will be realised that other means for curving the sheet could be used to obtain the benefits of the invention.

The light source (or 'illuminating means') is preferably a flash or strobe light so that the effect of movement of paper during image capture may be minimized.

The camera (or 'capturing means') may be a digital camera and may be a standard video camera employing a 2-dimensional charge coupled device (CCD) detector or photodiode array. Alternatively, the capturing means could be a line-scan camera with the image being generated by movement of the roller assembly. In a further alternative the capturing means could be a 1-dimensional CCD or photodiode array and the illuminated region of the sheet being imaged by means of a cylindrical lens. In all cases the image can be transferred to the processor either directly such as via a digital interface or indirectly such a by means of a frame grabber or analog to digital converter.

The sheet-surface analyser may also be used analyse other aspects of the sheet-surface and is not limited to analysing roughness. For example, with appropriate magnification, the shadows of pores in the surface can be imaged, and standard image analysis routines can be applied, such as thresholding and blob analysis, to construct a pore size distribution. Typically, a suitable threshold is chosen based on a visual criteria and is kept fixed for subsequent measurements so that comparative measurements can be made for different samples. Intensity values that are below the threshold are set to 0 (black) and values equal to and above the threshold are set to 255 (white). The thresholded image may then be segmented into regions by techniques such as 'blob analysis' with the pixel areas of each blob being accumulated into a histogram whose bins correspond to area intervals.

The pore structure of the paper may also be analysed in some circumstances, where the fibres which are lint candidates partially protrude from the paper surface. The shadow image is magnified and then at least one binary threshold of the image is created. A threshold is selected after examining the statistics of the brightness variation of the image. The threshold is selected at a specific number of standard deviations above or below the average intensity and held constant for other samples so that inter-sample comparisons can be reliably made.

The analysis of the captured image involves a binary threshold algorithm which manipulates the captured image to produce an analysing image in which pore shadows which are darker than the threshold value are converted to black and regions of the image outside the pores (which exceed the threshold) are converted to white. The number, sizes and shapes of the black regions are then measured using 'blob analysis' algorithms and stored as size and shape distributions, which are used to predict the pore characteristics of the paper sheet. In this way the analysing means analyses a characteristic of the image captured by the capturing means.

The linting propensities of the sheet-surface may also be analysed. 'Linting' of paper refers to the propensity of some paper fibres to rise above the plane of the sheet surface. These fibres can reduce print quality, and can separate from the sheet during printing, leading to a build-up of these fibres in the printing press. In this case, the analysis of the image involves a statistical comparison with regions or samples of sheet material which do not lint as a means to highlight regions in the sheet material of interest in which linting has occurred. The presence of, and magnitude of linting is determined by the excess number of dark shadows above the expected number of high intensity shadows expected from the measured roughness of the paper.

The word 'comprising' and forms of the word 'comprising' as used in this description do not limit the invention claimed to exclude any variants or additions.

Modifications and improvements to the invention will be readily apparent to those skilled in the art. Such modifications and improvements are intended to be within the scope of this invention.

The invention claimed is:

1. A sheet-surface analyser comprising:
   illuminating means for casting shadows on a sheet-surface;
   capturing means for capturing an image of the shadows;
   analysing means for analysing a captured shadow-image to thereby analyse the sheet-surface; and
   curving means for curving the sheet,
   wherein the illuminating means and the curving means are configured to enable the illuminating means to illuminate a curved part of the sheet-surface so that features of the sheet-surface cast shadows on the sheet-surface and the capturing means is configured to capture said shadow-image, the analysing means comprising a processor and a computer readable medium storing a computer program which when executed by the processor derives a matrix of rows and columns of light-intensity values from the captured shadow-image and calculates a sheet-surface value from the matrix wherein in calculating the sheet-surface value' deviation values of respective rows and columns are calculated, the deviation value being a measure of average deviation of the light intensity values in said row or column from a mean value in said row or column, and wherein a selected region of the matrix comprising one row and/or column having a maximum deviation value is weighted to contribute more to the sheet-surface value than a remainder of the matrix.

2. A sheet-surface analyser according to claim 1 wherein the curving means is a curved surface around which at least part of the sheet is locatable.

3. A sheet-surface analyser according to claim 2 wherein the curved surface forms part of a cylindrical drum.

4. A sheet-surface analyser according to any one of claims 1 to 3, further comprising advancing means for advancing the sheet towards and locating the sheet around the curving means.

5. A sheet-surface analyser according to claim 4 wherein the advancing means is at least one roller located relative to the curving means such that a sheet placed between the roller and the curving means is advanced by action of the or each roller towards and around the curving means.

6. A sheet-surface analyser according to claim 4 where the advancing means applies tension to the sheet as it is located around the curving means.

7. A sheet-surface analyser according to claim 4 wherein the curving means, illuminating means, capturing means and advancing means are contained within a casing having an aperture, having an arrangement being such that a sheet inserted into the aperture, is advanced towards and around the curving means, analysed and advanced out of the casing.

8. A sheet-surface analyser according to claim 7 further comprising a display associated with the casing for receiving input parameters related to the sheet-surface analysis and for visually displaying analysis results.

9. A sheet-surface analyser according to claim 1 wherein the sheet-surface value is calculated from a weighted sum of deviation values calculated for each row and/or colunm, the weight for each row and/or column being in proportion to the deviation value for that row or column, wherein each row or column contributes to the sheet-surface value in proportion to its deviation value.

10. A sheet-surface analyser according to claim 9 wherein the sheet-surface value is a mean of:
   a mean of weighted deviation values calculated for each matrix row; and
   a mean of weighted deviation values calculated for each matrix column.

11. A sheet-surface analyser according to claim 1 wherein the computer program comprises means for correcting the captured image for non-uniformity of illumination before calculating the sheet-surface value.

12. A sheet-surface analyser according to claim 11 wherein the means is computer program code for best fitting a low-order polynomial to elements of each matrix row and subtracting each elements from a value of the fitted polynomial at said element.

13. A sheet-surface analyser according to claim 1 wherein the sheet surface value represents a roughness of the sheet.

14. A method of analysing a sheet surface comprising the steps of:
   curving the sheet;
   casting a shadow on a surface of the curved sheet by illuminating the sheet;
   capturing an image of the shadow; and
   analysing a captured shadow-image by deriving a matrix of rows and columns of light-intensity values from the captured shadow-image, and calculating a sheet-surface value from the matrix, wherein in calculating the sheet-surface value, deviation values of respective rows and columns are calculated, the deviation values being a measure of average deviation of the light intensity values in said row or column from a mean value in said row or colunm, and wherein a selected region of the matrix comprising one row and/or column having a maximum devation value is weighted to contribute more to the sheet-surface value than a remainder of the matrix.

15. A method according to claim 14 further comprising the steps of:
   progressively advancing the sheet over a curved surface; and
   capturing an image of the shadow cast on the sheet surface at predetermined intervals.

16. A method according to claim 15 further comprising the step of correcting the matrix for non-uniform illumination before calculating the sheet-surface value.

17. A method according to claim 16 wherein the step of correcting the matrix comprises the steps of:
   best fitting a low-order polynomial to the-elements of each row of the matrix; and
   subtracting from each element the value of the best-fifed polynomial at said element.

18. A method according to claim 14 wherein the step of calculating a sheet-surface value comprises the steps of:
   calculating the deviation value for each matrix row and/or colunm;
   multiplying each deviation value by a weight that is in proportion to the deviation value; and
   averaging the weighted deviation values to calculate the sheet-surface value,
   wherein each row or column contributes to the sheet-surface value in proportion to its deviation value.

19. A method according to claim 18 further comprising the step of averaging average weighted deviation values for the matrix rows and average weighted deviation values for the matrix columns.

* * * * *